United States Patent
Wehner

(10) Patent No.: US 9,505,793 B2
(45) Date of Patent: Nov. 29, 2016

(54) AZINE METAL PHOSPHATES AS FLAME-RETARDANT MATERIALS

(71) Applicant: J.M. HUBER CORPORATION, Atlanta, GA (US)

(72) Inventor: Wolfgang Wehner, Zwingenberg (DE)

(73) Assignee: J.M. HUBER CORPORATION, Atlanta, GA (US)

( * ) Notice: Subject to any disclaimer, the term of this patent is extended or adjusted under 35 U.S.C. 154(b) by 0 days.

(21) Appl. No.: 14/436,329

(22) PCT Filed: Oct. 16, 2012

(86) PCT No.: PCT/EP2012/004329
§ 371 (c)(1),
(2) Date: Apr. 16, 2015

(87) PCT Pub. No.: WO2014/060003
PCT Pub. Date: Apr. 24, 2014

(65) Prior Publication Data

US 2015/0252065 A1 Sep. 10, 2015
US 2016/0137678 A9 May 19, 2016

(51) Int. Cl.

| | | |
|---|---|---|
| C08K 5/34 | (2006.01) | |
| C08K 5/3492 | (2006.01) | |
| C09K 21/00 | (2006.01) | |
| C07F 9/80 | (2006.01) | |
| C07F 9/09 | (2006.01) | |
| C07C 277/00 | (2006.01) | |
| C07C 279/00 | (2006.01) | |
| C07F 9/6521 | (2006.01) | |
| C07F 3/00 | (2006.01) | |
| C07F 3/02 | (2006.01) | |
| C07F 3/06 | (2006.01) | |
| C09K 21/12 | (2006.01) | |
| C07F 9/06 | (2006.01) | |
| C08K 5/52 | (2006.01) | |
| C08K 5/5313 | (2006.01) | |

(52) U.S. Cl.
CPC ............. *C07F 9/6521* (2013.01); *C07F 3/003* (2013.01); *C07F 3/02* (2013.01); *C07F 3/06* (2013.01); *C07F 9/06* (2013.01); *C08K 5/5205* (2013.01); *C08K 5/5313* (2013.01); *C09K 21/12* (2013.01)

(58) Field of Classification Search
None
See application file for complete search history.

(56) References Cited

U.S. PATENT DOCUMENTS

| 4,112,016 | A | 9/1978 | Moulds |
| 6,344,158 | B1 | 2/2002 | Schlosser et al. |
| 7,649,038 | B2 | 1/2010 | Dieter-Naegerl et al. |

| 2006/0089435 | A1 | 4/2006 | Hoerold et al. |
| 2008/0269384 | A1 | 10/2008 | Naegerl et al. |
| 2011/0245383 | A1 | 10/2011 | Dave et al. |
| 2014/0361230 | A1 | 12/2014 | Kostler et al. |

FOREIGN PATENT DOCUMENTS

| CN | 101693836 A | 4/2010 |
| CN | 101781571 A | 7/2010 |
| DE | 10 2007 036 465 A1 | 2/2009 |
| DE | 10 2010 035 103 A1 | 2/2012 |
| EP | 0 974 588 B1 | 1/2000 |
| EP | 1 024 166 A1 | 8/2000 |
| EP | 1 537 173 B1 | 6/2005 |
| EP | 1 789 475 B1 | 5/2007 |
| EP | 2 183 314 B1 | 5/2010 |
| WO | WO 97/44377 | 11/1997 |
| WO | WO 00/02869 | 1/2000 |
| WO | WO 2009/034023 A2 | 3/2009 |
| WO | WO 2010/057851 A1 | 5/2010 |
| WO | WO 2010/063623 A1 | 6/2010 |
| WO | WO 2012/025362 A1 | 3/2012 |

OTHER PUBLICATIONS

Ayyappan et al. "Synthesis and Structural Characterization of a Chiral Open-Framework Tin (II) Phosphate, [CN$_3$H$_6$] [Sn4P3O12] (GUAN-SnP0)", Chem. Mater., vol. 10, no. 11, Oct. 17, 1998 (Oct. 17, 1998), pp. 3308-3310, XP002687806, ISSN: 0897-4756.

Beletskaya et al., Arylation of 6H-Dibenzo[c,e][1,2$\lambda^5$] oxaphosphinine 6-Oxide, Russ. J. Org. Chem. 2004, 40(12), pp. 1782-1786.

Beyer, Dr. G.; Flame retardancy of PVC nanocomposites & nanocomposite based cables and he Eropean regulation CPD, Konf. Fire Resistance in Plastics, Nov. 19-21, 2007, 18 pages.

Harrison et al.; Hydrothermal Syntheses and Single-Crystal Structures of Some Novel Guanidinium-Zinc-Phosphates, Chem. Mater., 1997, 9, pp. 1837-1846.

Harrison et al.; $(CN_4H_7)_2$ $Zn_3(HPO_3)_4$, a three-dimensional framework zincophosphite: an example of template-template co-operation?, International Journal of Inorg. Mater., 2001, 3, pp. 1033-1038.

Harrison et al.; $(CN_3H_6)_2$ $Zn(HPO_3)_2$; An open-framework zincophosphite built up from phlyheral 12 rings, JCS Dalton Trans. 2001, pp. 2459-2461.

Harrison et al.; Pseudopyramidal Building Units in Mixed Inorganic/Organic Network Solids: Syntheses, Structures, and Properties of α- and β-$ZnHPO_3.N_4C_2H_4$, Inorg. Chem., 2001, 40, pp. 895-899.

Jensen et al., New Amine-Templated Zinc Phosphates with a Temperature-Induced Increase of Structural Dimensionality, Inorg. Chem., 2005, 44, pp. 658-665.

Mandal et al., Hydrothermal Synthesis and Structures of Three-Dimensional Zinc Phosphates Built-Up from Two-Dimensional Layers and One-Dimensional Chains and Ladders, Crystal Growth and Design, 2002, 2(6), pp. 665-673.

(Continued)

Primary Examiner — Susannah Chung
Assistant Examiner — Robert T Butcher
(74) Attorney, Agent, or Firm — Sutherland Asbill & Brennan LLP

(57) ABSTRACT

The present invention relates to azine metal phosphates, compositions containing the same, a process for preparing the same and their use as flame retardants. Typical representatives are $(A-H)^{(+)}[MtPO_4]^{(+)} \cdot 2H_2O$ and $(Mel-H)^{(+)} [AlP_2O_7]^{(+)}$ (where A=melamine or guanidine, Mel=melamine and Mt=Mg or Zn).

20 Claims, No Drawings

(56) References Cited

OTHER PUBLICATIONS

Suvitha et al., "Synthesis, growth, structural, spectroscopic and optical studies of a semiorganic NLO crystal: zinc guanidinium phosphate", Spectrochimica Acta, Part A: Molecular and Biomolecular Spectroscopy, vol. 86, Feb. 2012 (Feb. 2012), pp. 266-270, XP002687808, ISSN 1386-1425.

Database WPI Week 201071 Thomson Scientific, London, GB; AN 2010-K68146, XP002687804; & CN 101 781 571 A (Univ Suzhou Sci&Technology) Jul. 21, 2010 (Jul. 21, 2010) abstract, 2 pages.

Database WPI Week 201030 Thomson Scientific, London, GB; AN 2010-E60357 XP002687805; & CN 101 693 836 A (Univ Suzhou Sci&Technology) Apr. 14, 2010 (Apr. 14, 2010) abstract, 2 pages.

Wilkie et al., "Fire Retardancy of Polymeric Materials", Chapter 6, $2^{nd}$ edition (2010), CRS Press, FL, USA, pp. 129-162.

Chapters 5, Current Practice and Recent Commercial Developments in Flame Retardancy of Polyamides, authors: E. Weil and S. Levchik, Hanser Verlag, Munich, pp. 85-104.

Chapter 6, "Flame Retardants for Plastics and Textiles", (2009), authors: E. Weil and S. Levchik, Hanser Verlag, Munich, pp. 106-119.

AZINE METAL PHOSPHATES AS FLAME-RETARDANT MATERIALS

CROSS-REFERENCE TO RELATED APPLICATION(S)

This application is a National Phase Patent Application and claims priority to and the benefit of International Application Number PCT/EP2012/004329, filed on Oct. 16, 2012, the entire disclosure of which is incorporated herein by reference.

The present invention relates to azine metal phosphates, compositions containing the same, a process for preparing the same and their use as intumescent metal-containing flame retardants. Typical representatives are $(A\text{-}H)^{(+)}[MtPO_4]^{(-)}\cdot 2H_2O$ and $(Mel\text{-}H)^{(+)}[AlP_2O_7]^{(-)}$ (where A=melamine or guanidine, Mel=melamine and Mt=Mg or Zn).

BACKGROUND AND TECHNICAL OBJECT OF THE INVENTION

It is known that intumescent materials have a flame-retardant effect by foaming when strongly heated, e.g. in the presence of a fire, to form an insulating layer which does not burn lightly and in this way suppress, inter alia, the dripping of molten, possibly burning material.

Intumescent metal-containing melamine phosphates are already known from EP 2 183 314 B1. However, these have the disadvantage of a lack of thermal stability. Thus, for example, the aluminum salt $[(Mel\text{-}H)]_3^{(+)}[Al(HPO_4)_3]^{(3-)}$ described there gives off one mole of melamine and two moles of water under thermal treatment at 280 to 300° C., forming $[(Mel\text{-}H)]_2^{(+)}[AlP_3O_{10}]^{(2-)}$. A similar situation applies to $[(Mel\text{-}H)]_2^{(+)}[MgP_2O_7]^{(2-)}$. Furthermore, the products described there can be obtained only in a multi-stage process. These compounds also all have a disadvantageous modulus (melamine/metal ratio) of 3 or 2.

Amine metal phosphates are likewise known, as described, for example, in *Inorg. Chem.*, 2005, 44, 658-665, and *Crystal Growth and Design*, 2002, 2(6), 665-673, but owing to their alkylamine content they have an unsatisfactory thermal stability and are therefore not suitable as flame retardants.

Cyanoguanidine (dicyandiamide) zinc phosphite is described in *Inorg. Chem.*, 2001, 40, 895-899, where the modulus (cyanoguanidine/zinc ratio) is 1. Guanidine zinc phosphates are not to be found in this publication. Aminoguanidine zinc phosphite is described in *Intern. J. of Inorg. Mater.*, 2001, 3, 1033-1038, where the modulus (aminoguanidine/zinc ratio) is 2:3. The synthesis is likewise carried out hydrothermally. Aminoguanidine zinc phosphates are not to be found in this document. A guanidine zinc phosphite is disclosed in *JCS Dalton Trans.* 2001, 2459-2461, where the modulus (guanidine/zinc ratio) is 2. Guanidine zinc phosphates having a modulus of 1 are not described.

Guanidine zinc phosphates are also disclosed in *Chem. Mater.*, 1997, 9, 1837-1846. However, these are prepared hydrothermally and additionally require long reaction times. In addition, these phosphates have a modulus (guanidine/zinc ratio) of 0.5, 2 and 3 and are therefore distinctly different from the azine metal phosphates of the invention, which all have a modulus of 1.

Metal-free intumescent melamine phosphates are likewise known. Thus, a number of processes for preparing melamine polyphosphates have been described, for example in WO 00/02869, EP 1 789 475, WO 97/44377 and EP 0 974 588.

However, preparation according to these processes is time-consuming and the processes are associated with a very high energy consumption because of the high reaction temperatures (340 to 400° C.). In addition, urea is used as further additive.

A melamine polyphosphate-based formulation which is already on the market is described in EP 1 537 173 B1.

In addition, there are already intumescent flame retardant systems which are based on melamine, e.g. on melamine salts of 3,9-dihydroxy-2,4,8,10-tetraoxa-3,9-diphosphaspiro[5,5]-undecane 3,9-dioxide (MAP) and on melamine salts of bis(1-oxo-2,6,7-trioxa-1-phosphabicyclo[2.2.2]octan-4-yl-methanol) phosphate (melabis).

Further intumescent systems are described in chapter 6, pages 129-162 "Fire Retardancy of Polymeric Materials", $2^{nd}$ edition (2010), editors: C. Wilkie, A. B. Morgan, CRS Press, FL, USA.

Flame retardants for polyamides (PA) and thermoplastic polyesters (PET/PBT) are described in detail in chapters 5 and 6, pages 85-119, "Flame Retardants for Plastics and Textiles", (2009), authors: E. Weil and S. Levchik, Hanser Verlag, Munich.

However, the flame retardants described in the prior art have the disadvantage that they frequently have an unsatisfactory flame retardant effect and are unsuitable, or have only limited suitability, for use in plastics, in particular thermoplastic plastics and elastomers in the electrical and electronics sector. In addition, some phosphorus-containing flame retardants influence the electrical conductivity and can thus, for example, have an adverse effect on the properties of a thermoplastic plastics provided with flame retardants in electrical components.

Despite the numerous publications known from the prior art, there continues to be a need for flame retardants having optimized properties and improved environmental compatibility.

It was therefore an object of the present invention to provide more effective flame retardants, in particular ones having improved secondary properties such as reduced acidity (higher pH values) and thereby a lower corrosivity and also lower conductivity, compared to the flame retardants known from the prior art.

In particular, it was an object of the present invention to provide flame retardants which have a high degree of intrinsic (thermal) stability and give a polymer excellent mechanical properties after incorporation of the flame retardant.

It is therefore an object of the present invention to provide such flame retardants. These should also be readily obtainable.

DESCRIPTION OF THE INVENTION

Azine Metal Phosphates

The object has surprisingly been achieved according to the present invention by the provision of azine metal phosphates of the general formula [I],

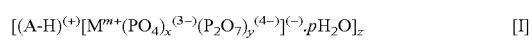

where $(A\text{-}H)^{(+)}$ is selected from among melamine-H of the formula (I), melam-H of the formula (II), guanamine of the formula (III), where R is methyl or phenyl, and (amino)guanidine-H of the formula (IV), where R is hydrogen or amine,

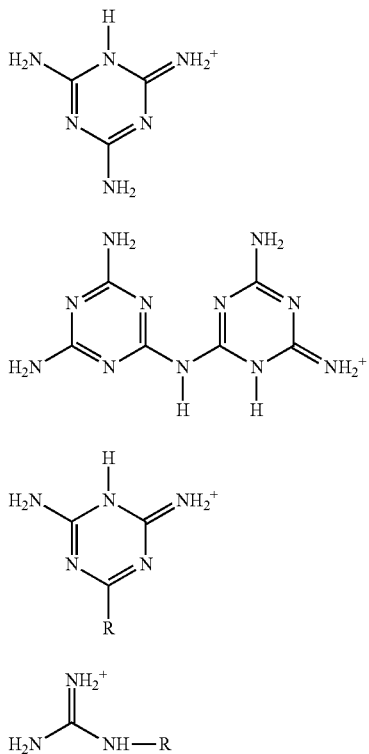

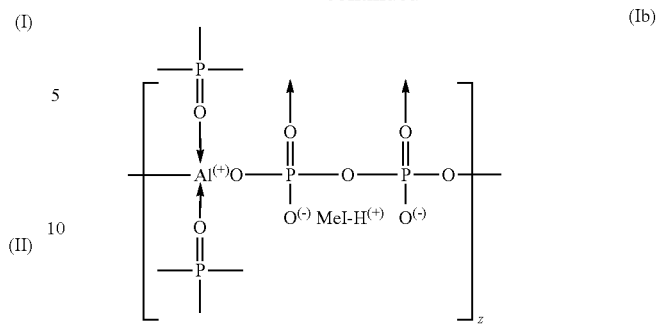

M is a metal or metal oxide selected from among Cu, Mg, Ca, Zn, Mn, Fe, Co, Ni, TiO, ZrO, VO, B, Si, Al, Sb, La, Ti, Zr, Ce, Bi and Sn, m=2 or 3, x and y are each, independently of one another, 0 or 1, p is an integer from 0 to 4 and z is an integer >5, where 1+m=3x+4y.

These compounds are preferably prepared by a non-hydrothermal route and have a modulus (azine/metal ratio) of 1.

The azine metal phosphates of the present invention are typically (coordination) polymers and can, as shown by the example of melamine zinc phosphate and melamine aluminum phosphate, be formulated with alternating (phosphate) $PO_4$ and $Zn(OP)_4$ tetrahedra or (diphosphate) $P_2O_7$ and $Al(OP)_4$ tetrahedra (structures Ia and Ib):

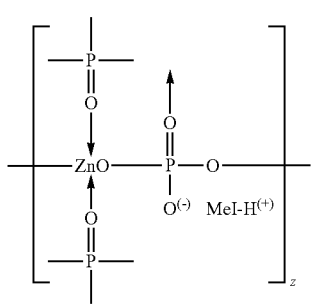

Preferred compounds are, for example:

$(A-H)^{(+)}[MtPO_4]^{(-)}\cdot pH_2O$, where A is melamine, guanidine or aminoguanidine, Mt is Mg or Zn and p is from 0 to 4;

$(A-H)^{(+)}[AlP_2O_7]^{(-)}$, where A is melamine, guanidine or aminoguanidine;

$(A-H)^{(+)}[MtPO_4]^{(-)}\cdot pH_2O$, where A is melam, acetoguanamine or benzoguanamine, Mt is Mg or Zn and p is from 0 to 4;

$(A-H)^{(+)}[AlP_2O_7]^{(-)}\cdot pH_2O$, where A is melam, acetoguanamine or benzoguanamine and p is from 0 to 4;

$(A-H)^{(+)}[MtPO_4]^{(-)}\cdot pH_2O$, where A is melamine, guanidine or aminoguanidine, Mt is Sn, TiO or ZrO and p is from 0 to 4;

$(A-H)^{(+)}[AlP_2O_7]^{(-)}\cdot pH_2O$, where A is melamine, guanidine or aminoguanidine, Mt is Ce, Sb or Bi and p is from 0 to 4.

It has surprisingly been able to be shown that the azine metal phosphates of the present invention are more thermally stable than conventional compounds used in flame retardants. In addition, they are simple to prepare in a single-stage process. The process for preparing them saves energy and is economical since the separate preparation of metal dihydrogenphosphates is dispensed with. This is advantageous particularly because metal dihydrogenphosphates are in the majority of cases only storage-stable when hot and tend to form a precipitate at room temperature after a certain time. However, these precipitates can be resolubilized only with difficulty.

Compositions Containing Azine Metal Phosphate

Furthermore, it has unexpectedly been found that the effect profile of the azine metal phosphates in respect of flame retardant effect and intumescence behavior can be optimized further by provision of compositions to which synergists or cocomponents have been added. These further components can be metal-containing or metal-free.

The present invention thus further provides a composition which comprises the above-described azine metal phosphates (component (i)), a further metal-containing component (ii) different from the component (i) and optionally a metal-free component (iii).

The additional metal-containing component (ii) can comprise, in particular, metal hydroxide, metal phosphate, metal pyrophosphate, hydrotalcite, hydrocalumite, cationically or anionically modified organoclay, stannate salt or molybdate salt, metal borate or metal phosphinate of the formula (V) or (VI) or metal phosphonate of the formula (VII),

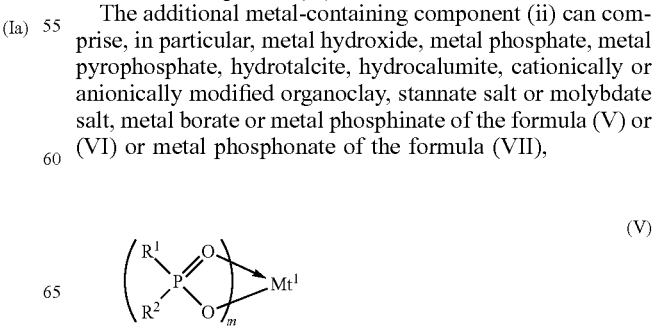

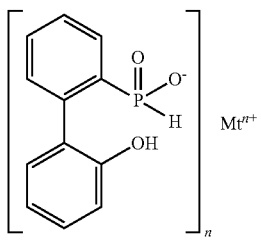

(VI)

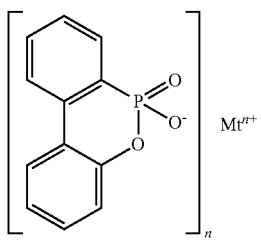

(VII)

where $R^1$ and $R^2$ are each, independently of one another, hydrogen, linear or branched $C_1$-$C_6$-alkyl or phenyl; $Mt^1$ is Ca, Mg, Zn or Al, m=2 or 3 and Mt is Ca, Mg, Zn, Al, Sn, Zr, TiO, ZrO, Ce, MoO, WO$_2$, VO, Mn, Bi or Sb, D=O or S and n is 2 or 3.

Hydrotalcite and hydrocalumite have, for example, the composition $Mg_6Al_2(OH)_{16}CO_3$ and $Ca_4Al_2(OH)_{12}CO_3$. To a person skilled in the art, organoclays are organophile-modified clay minerals (mainly montmorillonites) based on cation exchange, e.g. triethanol tallow ammonium montmorillonite and triethanol tallow ammonium hectorite, as described in Dr. G. Beyer; Konf. *Fire Resistance in Plastics*, 2007. Anionic organoclays are organophile-modified hydrotalcites based on anion exchange with alkali metal rosinates, unsaturated and saturated fatty acid salts and also long-chain alkyl-substituted sulfonates and sulfates.

Metal oxides are preferably diantimony trioxide, diantimony tetroxide, diantimony pentoxide or zinc oxide.

As metal phosphate, preference is given to metal pyrophosphates. Particular preference is given to aluminum pyrophosphate and zinc pyrophosphate and also zinc triphosphate and aluminum triphosphate and likewise aluminum metaphosphate and zinc metaphosphate and also aluminum orthophosphate and zinc orthophosphate.

Among cationically or anionically modified organoclays, the hydrotalcites modified with alkylsulfate or fatty acid carboxylate or clay minerals modified with long-chain quaternary ammonium are particularly preferred.

In the case of metal hydroxides, preference is given to magnesium hydroxide (brucite), aluminum trihydroxide (ATH, gibbsite) or aluminum monohydroxide (boehmite) and also hydromagnesite and hydrozincite. Apart from gibbsite and boehmite, mention may also be made of the other modifications of aluminum hydroxides, namely bayerite, nordstrandite and diaspore.

Furthermore, preferred molybdate salts or stannate salts are ammonium heptamolybdate, ammonium octamolybdate, zinc stannate or zinc hydroxystannate or mixtures thereof.

These also act as smoke reducers and therefore have particularly advantageous properties in the flame retardants of the present invention.

From the class of metal borates, preference is given to alkali metal borates, alkaline earth metal borates or zinc borate. Mention may also be made of aluminum borate, barium borate, calcium borate, magnesium borate, manganese borate, melamine borate, potassium borate, zinc borophosphate or mixtures thereof.

Metal phosphinates are preferably salts in which $Mt^1$ is selected from among Ca, Mg, Zn and Al. Preferred metal phosphinates are phenylphosphinate, diethyl(methyl, ethyl) phosphinate, in particular in combination with the above-mentioned metals.

Among hypophosphites, the Mg, Ca, Zn and Al salts are particularly preferred.

Preferred metal phosphinates (VI) and metal phosphonates (VII) are salts having Mt selected from among Ca, Mg, Zn and Al. Particular preference is given to using a metal phosphinate (VI) which is prepared from 6H-dibenz[c,e][1,2]oxaphosphorin 6-oxide [CAS No.: 35948-25-5) in water without use of alkali metal hydroxide. The use of metal phosphonates (VII) which are obtainable, for example, by thermal cyclization of precursors (VI) is also particularly preferred. Very particular preference is given to zinc or aluminum phosphonates and thiophosphonates (VII). The (thio)phosphonates are preferably prepared from the (thio) phosphonic acids (CAS No.: 36240-31-0 and CAS No.: 62839-09-2). All phosphorus precursors are obtainable as commercial products.

The metal-free (co)component (component (iii) of the composition of the invention) comprises, in particular, red phosphorus, oligomeric phosphate esters, oligomeric phosphonate esters, cyclic phosphonate esters, thiopyrophosphoric esters, melamine orthophosphate or melamine pyrophosphate, dimelamine phosphate, melam (polyphosphate), melem, ammonium polyphosphate, melamine phenylphosphonate and the monoester salt thereof, as described in WO 2010/063623, melamine benzenephosphinate as described in WO 2010/057851, hydroxyalkylphosphine oxides as described in WO 2009/034023, tetrakishydroxymethylphosphonium salts and phospholane (oxide) or phosphole derivatives and also bisphosphoramidates having piperazine as bridge member or a phosphinate ester, the class of NOR-HALS compounds (nonbasic amino ether hindered amine light stabilizers) and mixtures thereof.

As further additional components, preference is given to melamine polyphosphate, bismelamine zinc diphosphate, bismelamine magnesium diphosphate or bismelamine aluminum triphosphate.

Among oligomeric phosphate esters, preference is given to phosphate esters of the formula (VIII) or formula (IX),

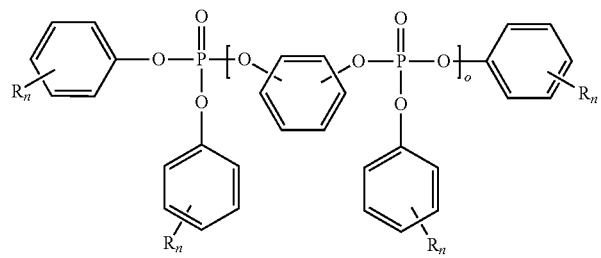

(VIII)

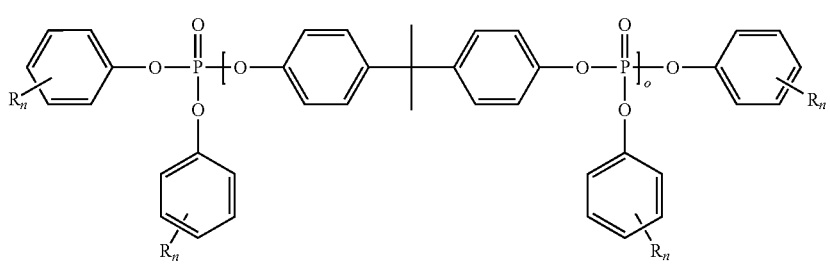

(IX)

where each R is independently hydrogen, $C_1$-$C_4$-alkyl or hydroxy, n=1 to 3 and o=1 to 10. Particular preference is given to oligomers having $R_n$=H and resorcinol or hydroquinone as constituent of the bridge member and also $R_n$=H and bisphenol A or bisphenol F as constituent of the bridge member.

Preference is given to oligomeric phosphonate esters of the formula (X),

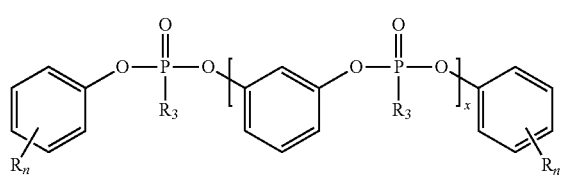

(X)

where $R_3$ is methyl or phenyl, x=1 to 20, R is in each case independently hydrogen, $C_1$-$C_4$-alkyl or hydroxy, n=1 to 3 and o is from 1 to 10. Particular preference is given to oligomers having $R_n$=H and resorcinol or hydroquinone as constituent of the bridge member.

Furthermore, preference is given to cyclic phosphonate esters of the formula (XI):

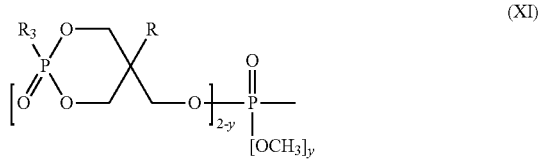

(XI)

where $R_3$ is methyl or phenyl, R is hydrogen or $C_1$-$C_4$-alkyl and y is 0 or 2. Bis[(5-ethyl-2-methyl-1,3,2-dioxaphosphorinan-5-yl)methyl]methylphosphonate P,P'-dioxide is particularly preferred.

Preference is also given to thiopyrophosphoric esters of the formula (XII)

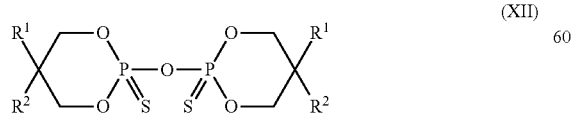

(XII)

where each $R^1$ and $R^2$ is independently hydrogen or $C_1$-$C_4$-alkyl. 2,2'-Oxybis[5,5-dimethyl-1,3,2-dioxaphosphorinan]2,2'-disulfide is particularly preferred.

Among the hydroxyalkylphosphine oxides, preference is given to isobutylbishydroxy-methylphosphine oxide and its combination with epoxy resins, as described in WO-A 2009/034023.

Among the tetrakishydroxyalkylphosphonium salts, the tetrakishydroxymethylphosphonium salts are particularly preferred.

Among the phospholane or phosphole derivatives, dihydrophosphole (oxide) derivatives and phospholane (oxide) derivatives and also salts thereof, as described in EP 1 024 166, are particularly preferred.

Among the bisphosphoramidates, the bis-di-ortho-xylyl esters having piperazine as bridge member are particularly preferred.

Particular preference is likewise given to phosphinate esters such as benzenemonophenyl ester derivatives or 9,10-dihydro-9-oxa-10-phosphaphenanthrene 10-oxide (6H-dibenzo(c,e)(1,2)-oxaphosphorin-6-one) derivatives as shown in the following formulae:

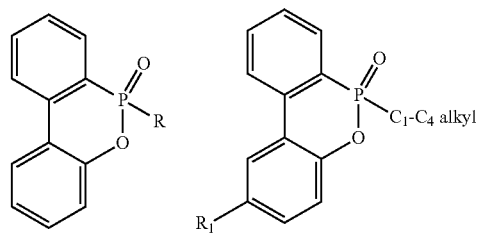

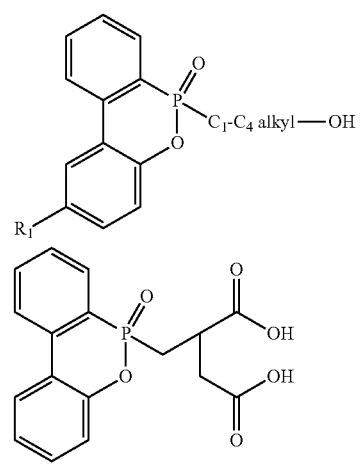

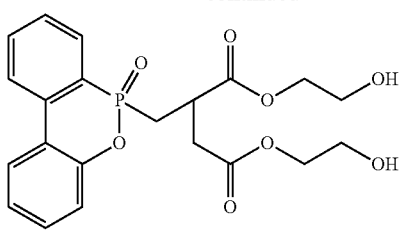
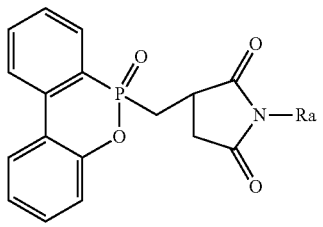
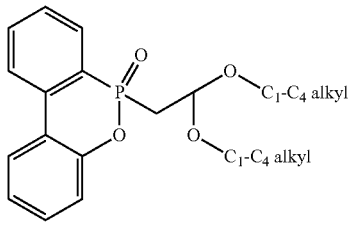
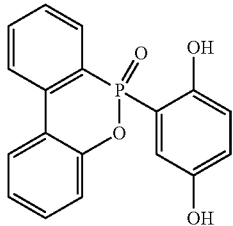
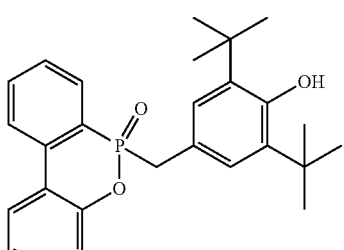
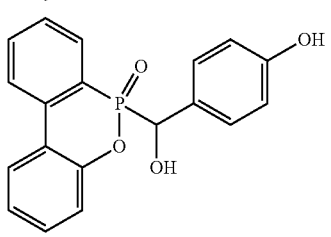
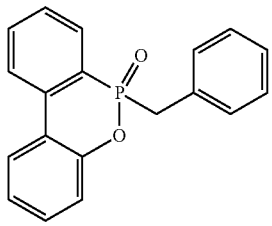
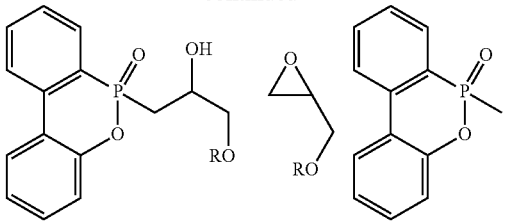
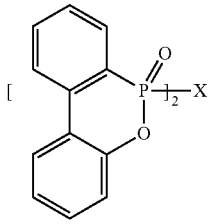
$X=(CH_2)_y$, where y=2-18.
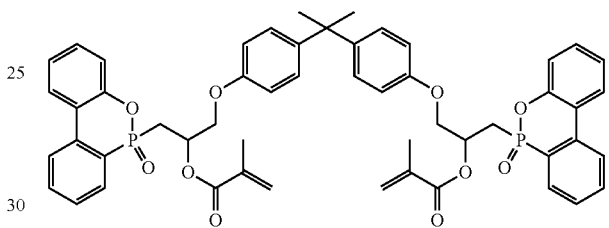
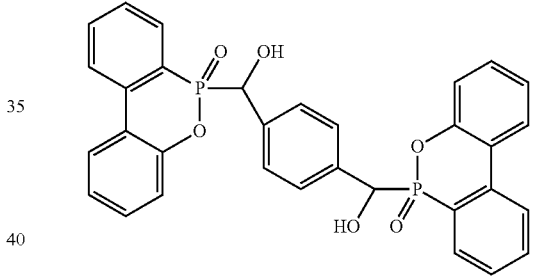
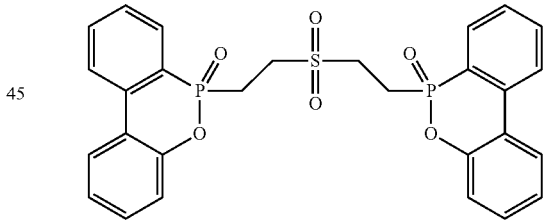
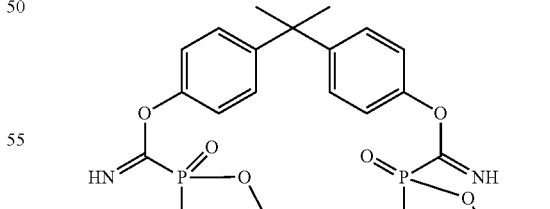
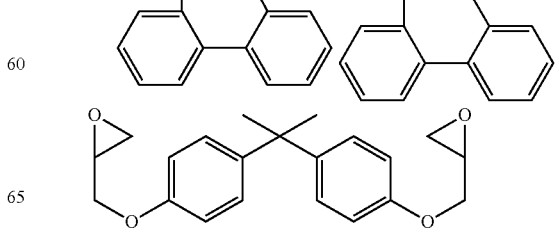

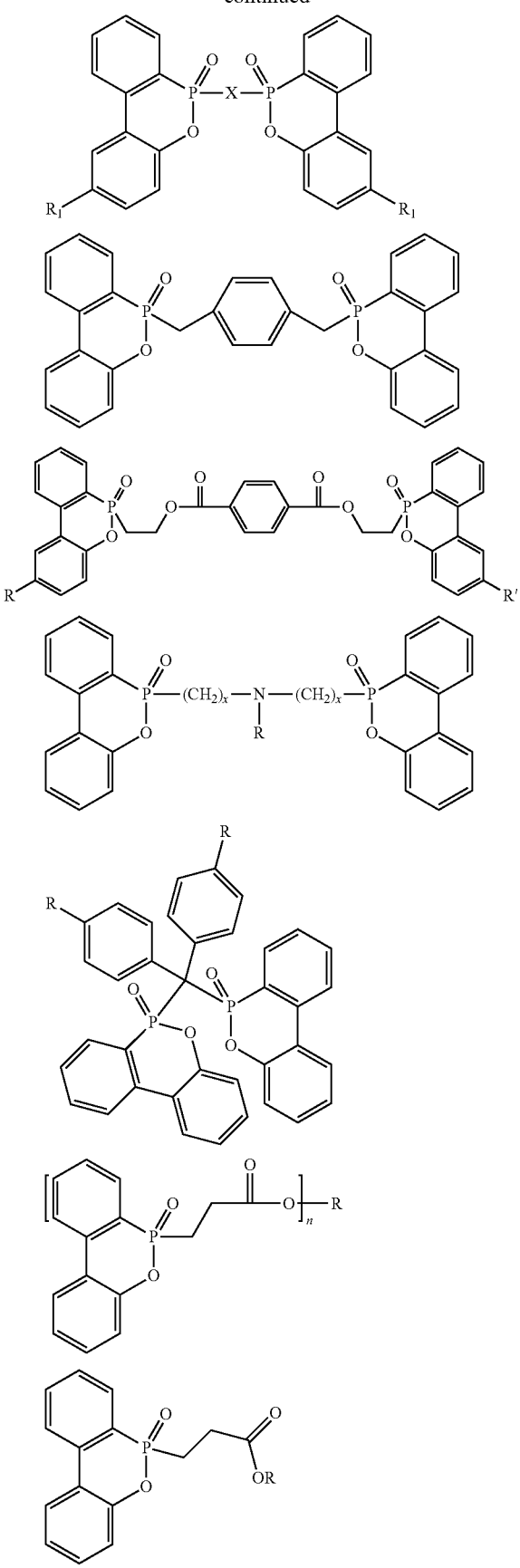

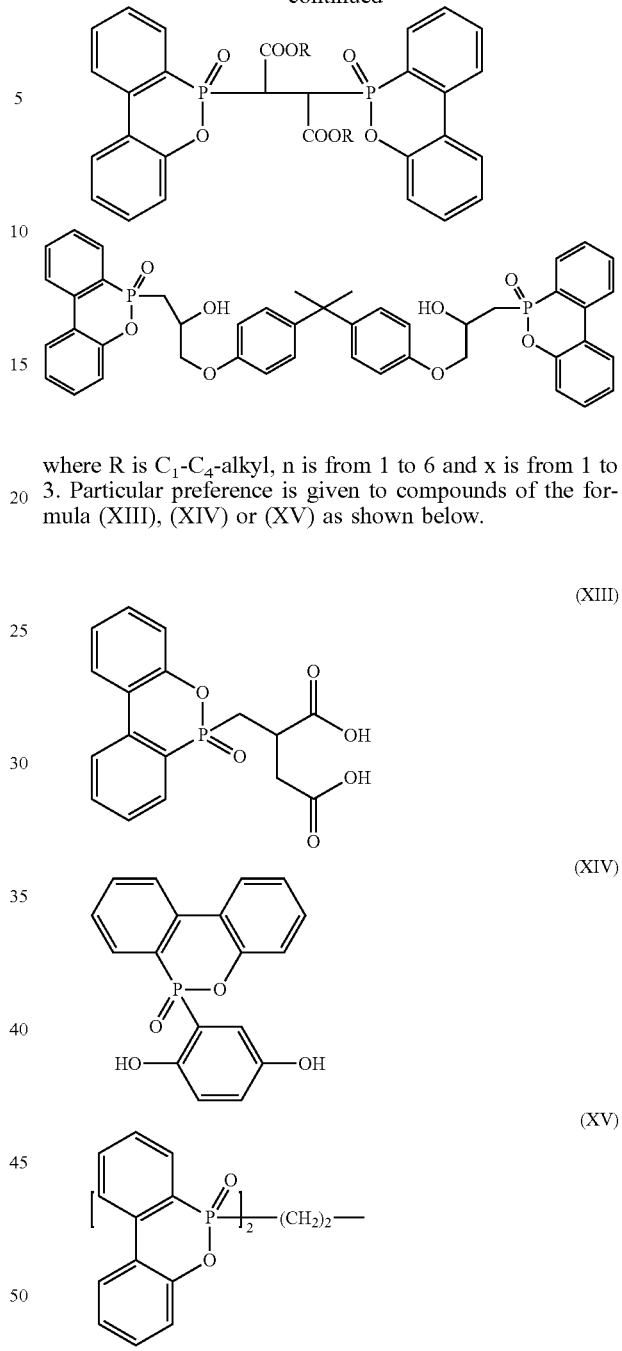

where R is $C_1$-$C_4$-alkyl, n is from 1 to 6 and x is from 1 to 3. Particular preference is given to compounds of the formula (XIII), (XIV) or (XV) as shown below.

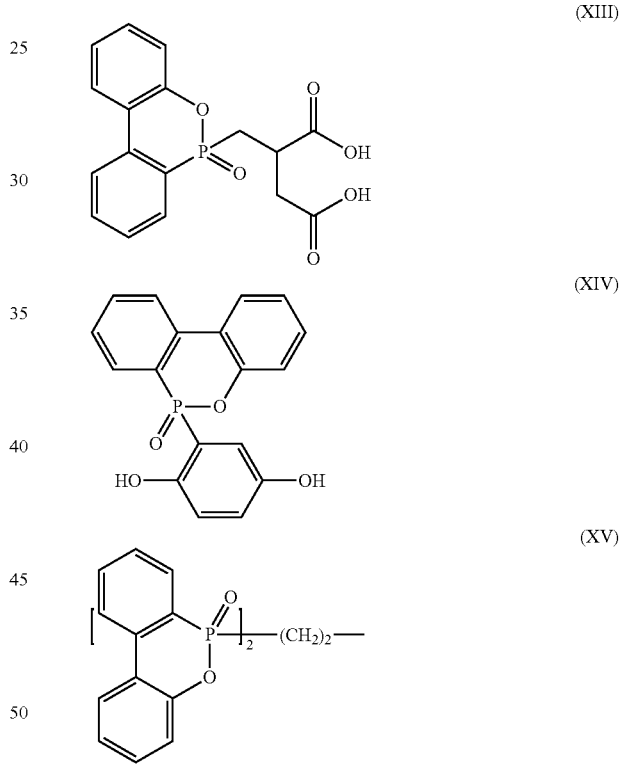

bis-9,10-Dihydro-9-oxa-10-phosphaphenanthrene 10-oxide (6H-dibenz[c,e][1,2]oxaphosphorin 6-oxide) compounds (formula XV) and 10-benzyl-9-oxa-10-phosphaphenanthrene 10-oxide, CAS No.: 113504-81-7. The preparation of these compounds is described in Russ. J. Org. Chem. 2004, 40(12), 1831-35. Further 9,10-dihydro-9-oxa-10-phosphaphenanthrene 10-oxide (6H-dibenz[c,e][1,2]oxaphosphorin 6-oxide) derivatives suitable for the purposes of the present invention are described in U.S. Pat. No. 8,101,678 B2 and U.S. Pat. No. 8,236,881 B2.

Instead of 9,10-dihydro-9-oxa-10-phosphaphenanthrene 10-oxide (6H-dibenz[c,e][1,2]oxaphosphorin 6-oxide), it is also possible to use dihydrooxaphosphaanthracene oxid (one). An overview may be found in WO-A 2008/119693.

Among the NOR-HALS compounds, preference is given to the following compounds:
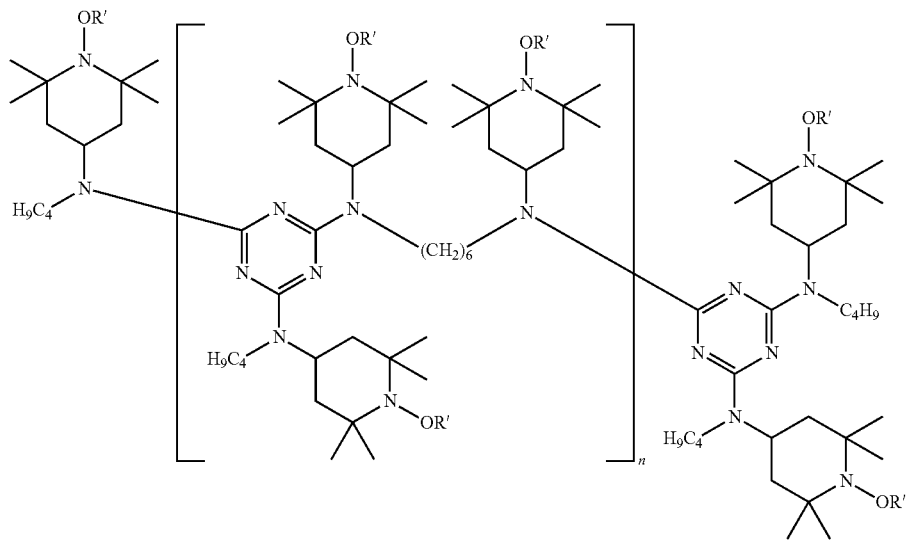
where R'=CH$_3$, n-C$_4$H$_9$ or c-C$_6$H$_{11}$
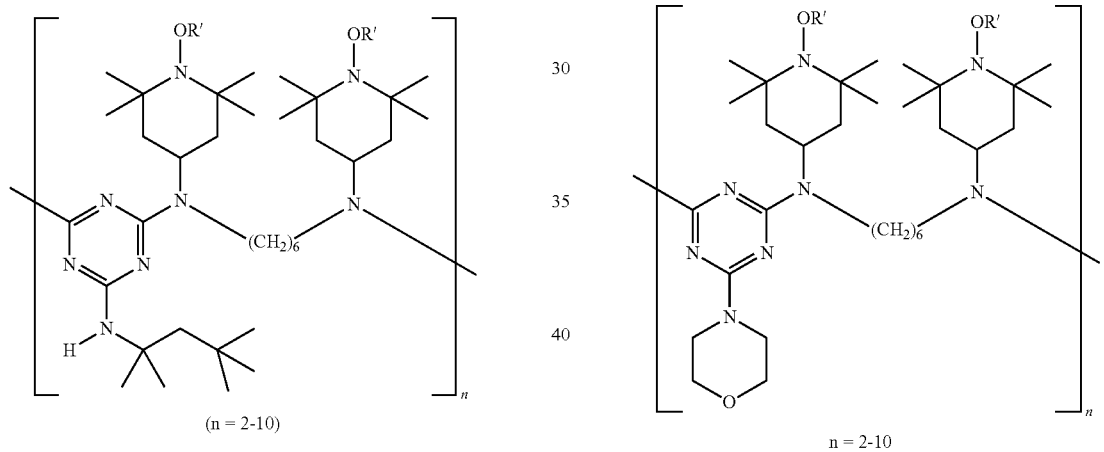
(n = 2-10)
where R'=CH$_3$, n-C$_4$H$_9$ or c-C$_6$H$_{11}$
n = 2-10
where R'=CH$_3$, n-C$_4$H$_9$ or c-C$_6$H$_{11}$
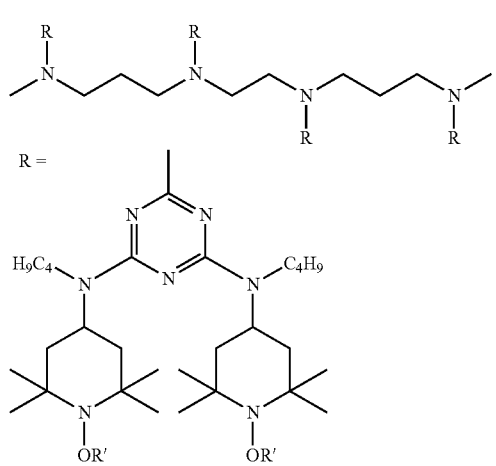
where R'=CH$_3$, n-C$_4$H$_9$ or c-C$_6$H$_{11}$
n = 2-10
where R'=CH$_3$, n-C$_4$H$_9$ or c-C$_6$H$_{11}$ In addition, polyols, aminouracils, POSS compounds, trishydroxyethyl isocyanurate, melamine cyanurate, expandable graphite or mixtures thereof are likewise preferred. POSS compounds (polyhedral oligomeric silsesquioxanes) and derivatives thereof are described in more detail in POLYMER, vol. 46, pp. 7855-7866. POSS derivatives based on methylsiloxane are particularly preferred here.

Furthermore, trishydroxyethyl isocyanurate polyterephthalates and triazine polymers having piperazin-1,4-diyl bridge members and morpholin-1-yl end groups can also be present in the flame retardants of the present invention.

Furthermore, the following additives can be present in the flame retardants of the present invention: bisazine pentaerythritol diphosphate salts, hexaaryloxytriphosphazenes, polyaryloxyphosphazenes and siloxanes, for example of the general formula $(R_2SiO)r$ or $(RSiO_{1.5})r$.

Mixtures of two or more of the above-described compounds can in principle also be present in the compositions of the present invention.

Particular preference is given to combinations of two such as:

MZP or $MAP_2$ (melamine zinc phosphate/melamine aluminum diphosphate) and

Mg (2'-hydroxy[1,1'-biphenyl-2-yl-2-phosphinate])$_2$ CAS No.: [165597-56-8],

Zn (2'-hydroxy[1,1'-biphenyl-2-yl-2-phosphinate])$_2$ CAS No.: [139005-99-5],

Al (2'-hydroxy[1,1'-biphenyl-2-yl-2-phosphinate])$_3$ CAS No.: [145826-41-1] as per formula (VI);

Mg (10-oxy-9,10-dihydro-9-oxaphosphaphenanthrene 10-oxidate)$_2$ CAS No.: [147025-23-8], Zn (10-oxy-9,10-dihydro-9-oxaphosphaphenanthrene 10-oxidate)$_2$ CAS No.: [69151-14-0], Al (10-oxy-9,10-dihydro-9-oxaphosphaphenanthrene 10-oxidate)$_3$ CAS No.: [121166-84-5], Ca (10-oxy-9,10-dihydro-9-oxaphosphaphenanthrene 10-oxidate)$_2$ CAS No.: [144722-45-2] as per formula (VII);

$M_2ZP_2$ or $M_2AP_3$ (dimelamine zinc diphosphate/dimelamine aluminum triphosphate) and Mg (2'-hydroxy[1,1'-biphenyl-2-yl-2-phosphinate])$_2$, Zn (2'-hydroxy[1,1'-biphenyl-2-yl-2-phosphinate])$_2$, Al (2'-hydroxy[1,1'-biphenyl-2-yl-2-phosphinate])$_3$, Mg (10-oxy-9,10-dihydro-9-oxaphosphaphenanthrene 10-oxidate)$_2$, Zn (10-oxy-9,10-dihydro-9-oxaphosphaphenanthrene 10-oxidate)$_2$ or Al (10-oxy-9,10-dihydro-9-oxaphosphaphenanthrene 10-oxidate)$_3$.

Very particular preference is given to combinations of three such as:

MZP or $MAP_2$ (melamine zinc phosphate/melamine aluminum diphosphate) and

Mg (2'-hydroxy[1,1'-biphenyl-2-yl-2-phosphinate])$_2$,

Zn (2'-hydroxy[1,1'-biphenyl-2-yl-2-phosphinate])$_2$,

Al (2'-hydroxy[1,1'-biphenyl-2-yl-2-phosphinate])$_3$,

Mg (10-oxy-9,10-dihydro-9-oxaphosphaphenanthrene 10-oxidate)$_2$,

Zn (10-oxy-9,10-dihydro-9-oxaphosphaphenanthrene 10-oxidate)$_2$ or

Al (10-oxy-9,10-dihydro-9-oxaphosphaphenanthrene 10-oxidate)$_3$; and zinc borate.

$M_2ZP_2$ or $M_2AP_3$ (dimelamine zinc diphosphate/dimelamine aluminum triphosphate) and Mg (2'-hydroxy[1,1'-biphenyl-2-yl-2-phosphinate])$_2$, Zn (2'-hydroxy[1,1'-biphenyl-2-yl-2-phosphinate])$_2$, Al (2'-hydroxy[1,1'-biphenyl-2-yl-2-phosphinate])$_3$, Mg (10-oxy-9,10-dihydro-9-oxaphosphaphenanthrene 10-oxidate)$_2$, Zn (10-oxy-9,10-dihydro-9-oxaphosphaphenanthrene 10-oxidate)$_2$ or Al (10-oxy-9,10-dihydro-9-oxaphosphaphenanthrene 10-oxidate)$_3$; and zinc borate.

MZP or $MAP_2$ (melamine zinc phosphate/melamine aluminum diphosphate) and

Mg (2'-hydroxy[1,1'-biphenyl-2-yl-2-phosphinate])$_2$,

Zn (2'-hydroxy[1,1'-biphenyl-2-yl-2-phosphinate])$_2$,

Al (2'-hydroxy[1,1'-biphenyl-2-yl-2-phosphinate])$_3$,

Mg (10-oxy-9,10-dihydro-9-oxaphosphaphenanthrene 10-oxidate)$_2$,

Zn (10-oxy-9,10-dihydro-9-oxaphosphaphenanthrene 10-oxidate)$_2$ or

Al (10-oxy-9,10-dihydro-9-oxaphosphaphenanthrene 10-oxidate)$_3$; and zinc stannate.

$M_2ZP_2$ or $M_2AP_3$ (dimelamine zinc diphosphate/dimelamine aluminum triphosphate) and Mg (2'-hydroxy[1,1'-biphenyl-2-yl-2-phosphinate])$_2$, Zn (2'-hydroxy[1,1'-biphenyl-2-yl-2-phosphinate])$_2$, Al (2'-hydroxy[1,1'-biphenyl-2-yl-2-phosphinate])$_3$, Mg (10-oxy-9,10-dihydro-9-oxaphosphaphenanthrene 10-oxidate)$_2$, Zn (10-oxy-9,10-dihydro-9-oxaphosphaphenanthrene 10-oxidate)$_2$ or Al (10-oxy-9,10-dihydro-9-oxaphosphaphenanthrene 10-oxidate)$_3$; and zinc stannate.

MZP or $MAP_2$ (melamine zinc phosphate/melamine aluminum diphosphate) and

Mg (2'-hydroxy[1,1'-biphenyl-2-yl-2-phosphinate])$_2$,

Zn (2'-hydroxy[1,1'-biphenyl-2-yl-2-phosphinate])$_2$,

Al (2'-hydroxy[1,1'-biphenyl-2-yl-2-phosphinate])$_3$,

Mg (10-oxy-9,10-dihydro-9-oxaphosphaphenanthrene 10-oxidate)$_2$,

Zn (10-oxy-9,10-dihydro-9-oxaphosphaphenanthrene 10-oxidate)$_2$ or

Al (10-oxy-9,10-dihydro-9-oxaphosphaphenanthrene 10-oxidate)$_3$; and boehmite.

$M_2ZP_2$ or $M_2AP_3$ (dimelamine zinc diphosphate/dimelamine aluminum triphosphate) and Mg (2'-hydroxy[1,1'-biphenyl-2-yl-2-phosphinate])$_2$, Zn (2'-hydroxy[1,1'-biphenyl-2-yl-2-phosphinate])$_2$, Al (2'-hydroxy[1,1'-biphenyl-2-yl-2-phosphinate])$_3$, Mg (10-oxy-9,10-dihydro-9-oxaphosphaphenanthrene 10-oxidate)$_2$, Zn (10-oxy-9,10-dihydro-9-oxaphosphaphenanthrene 10-oxidate)$_2$ or Al (10-oxy-9,10-dihydro-9-oxaphosphaphenanthrene 10-oxidate)$_3$; and boehmite.

MZP+MPP and

Mg (2'-hydroxy[1,1'-biphenyl-2-yl-2-phosphinate])$_2$,

Zn (2'-hydroxy[1,1'-biphenyl-2-yl-2-phosphinate])$_2$,

Al (2'-hydroxy[1,1'-biphenyl-2-yl-2-phosphinate])$_3$,

Mg (10-oxy-9,10-dihydro-9-oxaphosphaphenanthrene 10-oxidate)$_2$,

Zn (10-oxy-9,10-dihydro-9-oxaphosphaphenanthrene 10-oxidate)$_2$ or

Al (10-oxy-9,10-dihydro-9-oxaphosphaphenanthrene 10-oxidate)$_3$.

$MAP_2$+MPP and

Mg (2'-hydroxy[1,1'-biphenyl-2-yl-2-phosphinate])$_2$,

Zn (2'-hydroxy[1,1'-biphenyl-2-yl-2-phosphinate])$_2$,

Al (2'-hydroxy[1,1'-biphenyl-2-yl-2-phosphinate])$_3$,

Mg (10-oxy-9,10-dihydro-9-oxaphosphaphenanthrene 10-oxidate)$_2$,

Zn (10-oxy-9,10-dihydro-9-oxaphosphaphenanthrene 10-oxidate)$_2$ or

Al (10-oxy-9,10-dihydro-9-oxaphosphaphenanthrene 10-oxidate)$_3$.

Use of the Azine Metal Phosphate of the Invention

A particular embodiment of the invention provides for the use of the azine metal phosphate of the invention as flame retardant in a polymer or a polymer mixture. The present invention therefore further provides compositions as described above which additionally contain a polymer or a polymer mixture. The above-described composition comprising the components (i), (ii) and optionally (iii) is preferably produced first and this composition is incorporated into the polymer or the polymer mixture.

The invention also provides a process for producing flame-retarded polymer molding compositions, characterized in that the stabilized flame retardants according to the invention are homogenized with the polymer pellets and possibly additives in the polymer melt at elevated temperatures in a compounding apparatus and the homogenized polymer strand is subsequently taken off, cooled and pelletized. The pellets obtained are, for example, dried at 90° C. in a convection oven.

The compounding apparatus is preferably from the group consisting of single-screw extruders, multizone screws or twin-screw extruders. Suitable compounding apparatuses are single-screw extruders, e.g. from Berstorff GmbH, Hanover, and/or Leistritz, Nuremberg, multizone screw extruders having three-zone screws and/or short compression screws, co-kneaders, e.g. from Coperion Buss Compounding Systems, CH-Pratteln, e.g. MDK/E46-11 D, and/or laboratory kneaders (MDK 46 from Buss, Switzerland with L=11 D); twin-screw extruders, e.g. from Coperion Werner Pfleiderer GmbH & Co. KG. Stuttgart (ZSK 25, ZSK 30, ZSK 40, ZSK 58, ZSK MEGAcompounder 40, 50, 58, 70, 92, 119, 177, 250, 320, 350, 380) and/or from Berstorff GmbH, Hanover, Leistritz Extrusionstechnik GmbH, Nuremberg; ring extruders, e.g. from 3+Extruder GmbH, Laufen, having a ring of from three to twelve small screws which rotate around a static core and/or planetary gear extruders, e.g. from Entex, Bochum and/or devolatilization extruders and/or cascade extruders and/or Maillefer screws; compounders having contrarotating twin screws, e.g. Complex 37 or 70 types from Krauss-Maffei Berstorff.

The polymer is typically a thermoplastic which is preferably selected from the group consisting of polyamide, polycarbonate, polyolefin, polystyrene, polyester, polyvinyl chloride, polyvinyl alcohol, ABS and polyurethane, or a thermoset which is preferably selected from the group consisting of epoxy resin (with hardener), phenolic resin and melamine resin.

It is also possible to use mixtures of two or more polymers, in particular thermoplastics and/or thermosets, in which the azine metal phosphate of the invention is used as flame retardant.

Examples of such polymers are:
polymers of monoolefins and diolefins, e.g. polypropylene, polyisobutylene, poly-1-butene, poly-4-methyl-1-pentene, polyvinylcyclohexane, polyisoprene or polybutadiene, and polymers of cycloolefins, e.g. of cyclopentene or norbornene and polyethylene (also crosslinked), e.g. high density polyethylene (HDPE) or high molecular weight (HDPE-HMW), high density polyethylene having ultrahigh molecular weight (HDPE-UHMW), medium density polyethylene (MDPE), low density polyethylene (LDPE) and linear low density polyethylene (LLDPE), (VLDPE) and (ULDPE) and also copolymers of ethylene and vinyl acetate (EVA);

polystyrenes, poly(p-methylstyrene), poly(a-methylstyrene);

copolymers and graft copolymers of polybutadiene-styrene or polybutadiene and (meth)acrylonitrile, e.g. ABS and MBS;

halogen-containing polymers such as polychloroprene, polyvinyl chloride (PVC); polyvinylidene chloride (PVDC), copolymers of vinyl chloride-vinylidene chloride, vinyl chloride-vinyl acetate or vinyl chloride-vinyl acetate;

poly(meth)acrylates, polymethyl methacrylates (PMMA), polyacrylamide and polyacrylonitrile (PAN);

polymers of unsaturated alcohols and amines or acyl derivatives or acetals thereof, e.g. polyvinyl alcohol (PVA), polyvinyl acetates, stearates, benzoates or maleates, polyvinyl butyral, polyallyl phthalates and polyallylmelamines;

homopolymers and copolymers of cyclic ethers, e.g. polyalkylene glycols, polyethylene oxides, polypropylene oxides and copolymers thereof with bisglycidyl ethers;

polyacetals such as polyoxymethylenes (POM) and also polyurethane and acrylate-modified polyacetals;

polyphenylene oxides and sulfides and mixtures thereof with styrene polymers or polyamides;

polyamides and copolyamides derived from diamines and dicarboxylic acids and/or from aminocarboxylic acids or the corresponding lactams, e.g. polyamide 4, polyamide 6, polyamide 6/6, 6/10, 6/9, 6/12, 12/12, polyamide 11, polyamide 12, aromatic polyamides derived from m-xylylenediamine and adipic acid and copolyamides modified with EPDM or ABS. Examples of polyamides and copolyamides are derived from ε-caprolactam, adipic acid, sebacic acid, dodecanoic acid, isophthalic acid, terephthalic acid, hexamethylenediamine, tetramethylenediamine, 2-methylpentamethylenediamine, 2,2,4-trimethylhexamethylenediamine, 2,4,4-trimethylhexamethylenediamine, m-xylylenediamine or bis(3-methyl-4-aminocyclohexyl)methane;

polyureas, polyimides, polyamidimides, polyetherimides, polyesterimides, polyhydantoins and polybenzimidazoles;

polyesters derived from dicarboxylic acids and dialcohols and/or hydroxycarboxylic acids or the corresponding lactones, e.g. polyethylene terephthalate, polypropylene terephthalate, polybutylene terephthalate, poly-1,4-dimethylcyclohexane terephthalate, polyalkylene naphthalate (PAN) and polyhydroxybenzoates, polylactic esters and polyglycolic esters;

polycarbonates and polyester carbonates;

polyketones;

mixtures or alloys of polymers mentioned above, e.g. PP/EPDM, PA/EPDM or ABS, PVC/EVA, PVC/ABS, PBC/MBS, PC/ABS, PBTP/ABS, PC/AS, PC/PBT, PVC/CPE, PVC/acrylate, POM/thermoplastic PUR, PC/thermoplastic PUR, POM/acrylate, POM/MBS, PPO/HIPS, PPO/PA6.6 and copolymers, PA/HDPE, PA/PP, PA/PPO, PBT/PC/ABS or PBT/PET/PC, and TPE-O, TPE-S and TPE-E;

thermosets such as PF, MF or UF or mixtures thereof;

epoxy resins—thermoplastics and thermosets;

phenolic resins;

wood-plastic composites (WPC) and polymers based on PLA, PHB and starch.

The concentration of the flame retardant preparations according to the invention consisting of the azine metal phosphate (component (i)) and the additional metal-containing component (ii) and optionally the metal-free component (iii) in a polymer or a polymer mixture is preferably from 0.1 to 60% by weight, based on the polymer or the polymer mixture. The component ratio of azine metal phosphate (i) to the cocomponents (ii) and optionally (iii) in the composition is preferably in the range from 1:1 to 1:4.

In a preferred embodiment of the invention, the polymer material of the invention can contain further fillers which are preferably selected from the group consisting of metal hydroxides and/or metal oxides, preferably alkaline earth metal hydroxides, for example magnesium hydroxide, and aluminum hydroxide, silicates, preferably sheet silicates such as bentonite, kaolinite, muscovite, pyrophyllite, marcasite and talc, or other minerals such as wollastonite, silicon dioxide such as quartz, mica, feldspar, and also titanium dioxide, alkaline earth metal silicates and alkali metal silicates, carbonates, preferably calcium carbonate, also talc, clay, mica, diatomaceous earth, calcium sulfate, barium sulfate, pyrite, glass fibers, glass particles, glass beads and glass spheres, wood flour, cellulose powder, carbon black, graphite, chalk and pigments.

These fillers can give the polymer material further desired properties. In particular, the mechanical stability can be increased by, for example, reinforcement with glass fibers or the polymer can be colored by addition of dyes.

In a further embodiment, the polymer materials can contain further additives such as antioxidants, light stabilizers, processing aids, nucleating agents, antistatics, lubricants such as calcium stearate and zinc stearate, viscosity improvers, impact modifiers and in particular compatibilizers and dispersants.

Furthermore, foam formers can be added to the polymer in addition to the azine metal phosphate according to the invention. Foam formers are preferably melamine, melamine-formaldehyde resins, urea derivatives such as urea, thiourea, guanamines, benzoguanamines, acetoguanamine and succinylguanamine, dicyandiamide, guanidine and guanidine sulfamate and also other guanidine salts or allantoins and glycolurils.

In addition, a polymer containing the azine metal phosphate of the invention can also contain antidripping agents, in particular ones based on polytetrafluoroethylene. The concentration of such antidripping agents is preferably from 0.01 to 15% by weight, based on the polymer to be processed.

Process for preparing azine metal phosphates according to the invention

The invention also provides a process for preparing the above-described azine metal phosphates according to the invention by reacting an azine starting material (A) with a metal oxide starting material (B) and orthophosphoric acid (C), wherein the azine starting material (A) is selected from among melamine of the formula (I-H), melam of the formula (II-H), guanamine of the formula (III-H) and guanidine (bi)carbonate of the formula (IV-H) and the metal oxide starting material (B) is selected from among metal oxides, metal hydroxides and/or metal carbonates.

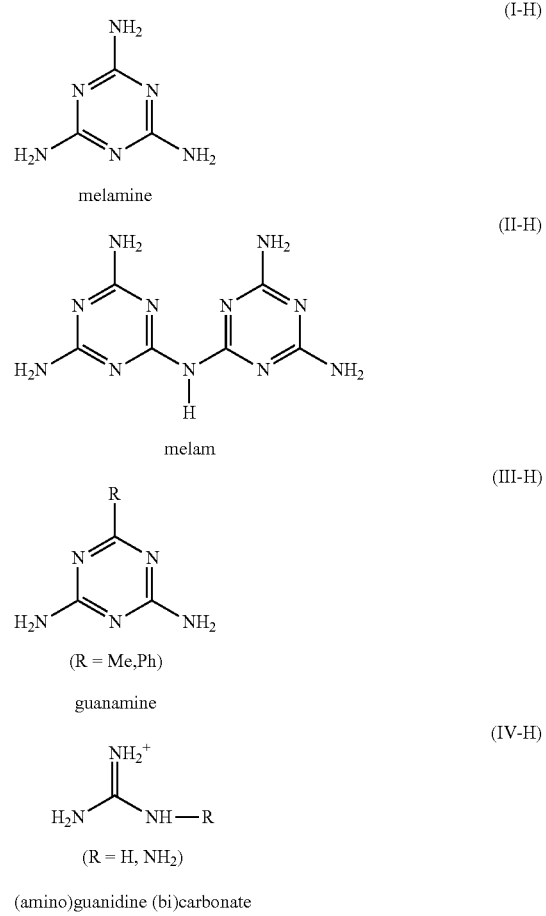

Preferred azine starting materials are melamine, guanamine and melam. Preferred metal oxides are selected from among MgO, ZnO, $Al_2O_3$ and SnO, $ZrO_2$, preferred metal hydroxides are selected from among $Mg(OH)_2$, $Zn(OH)_2$, $Al(OH)_3$, $Ce(OH)_3$ and $Bi(OH)_3$ and (basic) metal carbonates are preferably selected from among $CaCO_3$, $MgCO_3$, basic magnesium carbonate (hydromagnesite), basic zinc carbonate and basic zirconium carbonate. Particular preference is given to $Mg(OH)_2$, ZnO, $Al(OH)_3$ and basic zinc carbonate. In principle, mixtures of two or more of the abovementioned compounds can also be used as azine starting material (A) and/or as metal oxide starting material (B).

The process usually comprises the following steps:
(a) initial charging of an aqueous suspension of azine component (A) and metal oxide starting material (B) (i.e. metal (hydr)oxide or (basic) metal carbonate),
(b) addition of orthophosphoric acid,
(c) heating to preferably 60-80° C.,
(d) isolation of the product and
(e) optionally drying to constant weight and/or tempering at typically 250-300° C.

The process preferably comprises reaction of the components (A-1 to A-4):(B):(C) in a molar ratio of (1 to 3):(1):(1 to 3), as a result of which it is, in particular, ensured that additional melamine phosphates or (amino)guanidine phosphates are formed in-situ.

Step (a) can particularly preferably be followed by a granulation process. This can preferably be carried out as spray agglomeration in a spray dryer, spray granulator (top spray or bottom spray, countercurrent process), fluidized-bed granulator or in a paddle mixer or horizontal dryer, with the water introduced being removed until the desired residual moisture content is obtained. The granulation can take place by spray drying of an aqueous suspension of an azine metal phosphate of the formula (I) at usually 70-80° C. or alternatively as spray granulation starting out from a feed mixture of components (A) and (B) as fluidized bed and spraying of component (C) onto the fluidized bed and subsequent drying. The fluidized bed temperature is kept constant in the range from 70-80° C., with the granules drying at the same time and a free-flowing, non-dusting granular material being formed. The residual water content is about 0.5-1%.

Tempering of the reaction product typically takes place at from 220 to 350° C., preferably from 250 to 300° C.

EXAMPLES

The following examples serve to illustrate the invention, with the compounds of examples 1 to 6 describing the process of the invention and examples 1 to 4 further describing novel compounds. Example 7 is a comparative example. Example 8 describes the use of the compounds of the invention as flame retardants.

Example 1

Synthesis of melamine magnesium phosphate dihydrate (MMP) $C_3H_7N_6O_4PMg.2H_2O$ (MW: 282.5)

127.4 g (1.01 mol) of melamine and 58.3 g (1.0 mol) of magnesium hydroxide are suspended in 1.5 l of water with stirring. 115.3 g (1.0 mol) of orthophosphoric acid (85% strength) are added dropwise as dilute aqueous solution to this suspension while stirring. After stirring at 60° C. for 1 hour, a voluminous precipitate is formed. The mixture is subsequently stirred for another 60 minutes, cooled to room temperature, the white precipitate formed is filtered off with suction, washed with water and dried to constant weight at 120° C.

Yield: 253.0 g corresponding to 90% of theory.
Elemental analysis:

| Found: | C: 12.70%; | H: 3.67%; | N: 29.69%; | Mg: 8.47%; | P: 10.87% |
|---|---|---|---|---|---|
| Calculated: | C: (12.80%); | H: (3.90%); | N: (29.80%); | Mg: (8.60%); | P: (11.0%) |

Example 2

Synthesis of melamine zinc phosphate dihydrate (MZP) $C_3H_7N_6O_4PZn.2H_2O$ (MW=323.5)

2547 g (20.2 mol) of melamine and 1628 g (20.0 mol) of zinc oxide are suspended in 20 l of water with stirring. 2306 g (20.0 mol) of orthophosphoric acid (85% strength) are added dropwise as dilute aqueous solution to this suspension while stirring. After stirring at 60° C. for 1 hour, a voluminous precipitate is formed. The mixture is subsequently stirred for another 60 minutes, cooled to room temperature, the white precipitate formed is filtered off with suction, washed with water and dried to constant weight at 120° C. (product 2-I).

Yield: 6042.0 g corresponding to 93.4% of theory.
Elemental analysis:

| Found: | C: 11.6%; | H: 2.83%; | N: 27.20%; | Zn: 19.83%; | P: 9.45% |
|---|---|---|---|---|---|
| Calculated: | C: (11.1%); | H: (3.4%); | N: (26.0%); | Zn: (20.2%); | P: (9.6%) |

The product 2-I obtained in this way was tempered at 290° C. for 4 hours (product 2-11), weight loss: 10.4%. $C_3H_7N_6O_4PZn$ (molecular weight: 287.5).
Elemental analysis:

| Found: | C: 12.37%; | H: 2.05%; | N: 27.48%; | Zn: 21.35%; | P: 10.28% |
|---|---|---|---|---|---|
| Calculated: | C: (12.53%); | H: (2.45%); | N: (29.23%); | Zn: (22.74%); | P: (10.77%) |

Example 3

Synthesis of guanidine magnesium phosphate hemihydrate (GMP) $CH_6N_3O_4PMg.0.5H_2O$ (MW=188.4)

91.0 g (0.505 mol) of bisguanidinium carbonate and 58.3 g (1.0 mol) of magnesium hydroxide are suspended in 1.5 l of water with stirring. 115.3 g (1.0 mol) of orthophosphoric acid (85% strength) are added dropwise as dilute aqueous solution to this suspension while stirring. After stirring at 35° C. for 1 hour, a white precipitate is formed. The mixture is subsequently stirred for another 60 minutes, cooled to room temperature, the white precipitate formed is filtered off with suction, washed with water and dried to constant weight at 120° C.

Yield: 109.1 g corresponding to 58% of theory.

Example 4

Synthesis of guanidine zinc phosphate (GZP) $CH_6N_3O_4PZn$ (MW=220.4)

91.0 g (0.505 mol) of bisguanidinium carbonate and 81.4 g (1.0 mol) of zinc oxide are suspended in 1.5 l of water with stirring. 115.3 g (1.0 mol) of orthophosphoric acid (85% strength) are added dropwise as dilute aqueous solution to this suspension while stirring. After stirring at 60° C. for 1 hour, a voluminous precipitate is formed.

The mixture is subsequently stirred for another 60 minutes, cooled to room temperature, the white precipitate formed is filtered off with suction, washed with water and dried to constant weight at 120° C.

Yield: 185.0 g corresponding to 84% of theory.

Example 5

Synthesis of dimelamine zinc bisphosphate monohydrate ($M_2ZP_2$) $C_6H_{16}N_{12}O_8P_2Zn.H_2O$ (MW=529.6)

2547 g (20.2 mol) of melamine and 814 g (10.0 mol) of zinc oxide are suspended in 15 l of water with stirring. 2306 g (20.0 mol) of orthophosphoric acid (85% strength) are added dropwise as dilute aqueous solution to this suspension while stirring. After stirring at 60° C. for 1 hour, a voluminous precipitate is formed. The mixture is subsequently stirred for another 60 minutes, cooled to room temperature, the white precipitate formed is filtered off with suction, washed with water and dried to constant weight at 120° C. (product 5-I).

Yield: 5118 g corresponding to 96.6% of theory.

The product 5-1 obtained in this way was tempered at 290° C. for 4 hours (product 5-II). Weight loss: 7.3%, with dimelamine zinc diphosphate resulting.

Elemental analysis:

| Found: | C: 14.67%; | H: 2.40%; | N: 33.58%; | Zn: 12.67%; | P: 12.34% |
|---|---|---|---|---|---|
| Calculated: | C: (14.6%); | H: (2.85%); | N: (34.05%); | Zn: (13.25%); | P: (12.55%) |

Example 6

Synthesis of dimelamine zinc bisphosphate monohydrate ($M_2ZP_2$) $C_6H_{16}N_{12}O_8P_2Zn \cdot H_2O$ (MW=529.6) by the spray process 2547 g of melamine (20.2 mol) and 814 g (10.0 mol) of ZnO are placed in a GPCG 3.1 fluidized-bed granulator from GLATT GmbH. The bed of solid is continuously fluidized by means of a stream of air and a solution produced from 2306 g (20.0 mol) of orthophosphoric acid in 1000 ml of water is sprayed onto it. The fluidized-bed temperature is kept constant in the range 70-80° C., with the granules drying at the same time and a free-flowing, non-dusting granular material being formed. The main fraction (>80%) has a particle size range of 200-400 μm. The residual water content is about 0.5-1%.

Yield: quantitative.

The product 6-I obtained in this way was tempered at 290° C. for 4 hours (product 6-II). Weight loss: 8.0%, with dimelamine zinc diphosphate resulting.

Elemental analysis:

| Found: | C: 14.06%; | H: 2.48%; | N: 33.64%; | Zn: 12.79%; | P: 11.98% |
|---|---|---|---|---|---|
| Calculated: | C: (14.6%); | H: (2.85%); | N: (34.05%); | Zn: (13.25%); | P: (12.55%) |

Comparative Example 7

Synthesis of dimelamine pyrophosphatozincate $[Mel-H]^+{}_2[ZnP_2O_7]^{2-}$ (as described in EP 2 183 314 B1)

Step I: Preparation of zinc bisdihydrogenphosphate:

81.37 g (1 mol) of ZnO are reacted with 230.6 g (2 mol) of orthophosphoric acid (85% strength) in about 500 ml of water while stirring. After stirring at 90° C. for 2 hours, the ZnO had reacted.

Step II: Reaction of zinc bisdihydrogenphosphate with melamine:

252.2 g of melamine are suspended in about 500 ml of water. The zinc bisdihydrogenphosphate (step I) is added while stirring and the product is filtered off and dried at 120° C.

Yield: 503.0 g corresponding to 95% of theory.

Step III: 200 g of product from step II are tempered at 300° C. for 3 hours. Weight loss: 6.5% pH measurements and conductivity of 10% strength aqueous suspensions were, after filtration, measured at room temperature on the experimental products (examples 1 to 7). Furthermore, TGA/DSC measurements (heating rate: 10 K/min; $N_2$/50) were carried out using a Netzsch STA 409 instrument (see table 1).

TABLE 1

Property data for the experimental products

| | pH values | |
|---|---|---|
| Example | Product I | Product II |
| 1 (MMP) | 6.97 | — |
| 2 (MZP) | 5.2 | 5.6 |
| 3 (GMP) | 10.1 | 8.48 |
| 4 (GZP) | 7.48 | 6.57 |
| 5 ($M_2ZP_2$) | 4.89 | 5.5 |
| 7 (comparative product*) | 4.54 | 5.5 |

*prepared as described in EP 2 183 314 B1

The following zinc compounds were examined further as flame retardants: (see table 2)

TABLE 2

Physical properties of zinc compounds

| | Conductivity [μS/cm] | | Weight loss at 300° C. in % |
|---|---|---|---|
| Example | Product I | Product II | Product II |
| 2 (MZP) | 136 | 138 | 0.5 |
| 4 (GZP) | 180 | 82 | 0.3 |
| 5 ($M_2ZP_2$) | 255 | 209 | 0.3 |
| 7 (comparative product*) | 490 | 560 | 0.6 |

The products 2, 4 and 5 according to the invention show improved conductivity values compared to the conductivity value of product 7. The weight losses at 300° C. are likewise lower than in the case of the comparative product 7.

Example 8

Use as Flame Retardant in PA

Materials: PA 6.6 (Durethan A30S; from LANXESS); glass fibers (ThermoFlow® 671; 10 μm×4 mm; from John Manville); melamine polyphosphate MPP (Melapur 200; from BASF), Zn (2'-hydroxy[1,1'-biphenyl-2-yl-2-phosphinate])$_2$ (in-house product), dimelamine zinc diphosphate (example 5).

The components were compounded and pelletized on a Leistritz ZSE 27HP-44D (φ=27 mm, 44 D) twin-screw extruder. Test specimens (d=1.6 mm) conforming to the standard were made from these pellets by injection molding. The burning test was carried out in accordance with the UL-94 test. The results are shown in table 3.

TABLE 3

Flame retardant test

| Components | A | B |
|---|---|---|
| PA 6.6 | 47.5% | 48.0% |
| Glass fibers | 30.0% | 30.0% |

TABLE 3-continued

Flame retardant test

| Components | A | B |
|---|---|---|
| Flame retardant components: | | |
| (2'-Hydroxy[1,1'-biphenyl-2-yl-2-phosphinate])$_2$Zn | 12.5% | 12.0% |
| MPP | — | 10.0% |
| M$_2$ZP$_2$ | 10.0% | — |
| UL-94 test | V-0 | V-0 |

The invention claimed is:

1. An azine metal phosphate of the general formula [I],

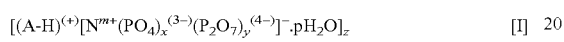

where $(A-H)^{(+)}$ is selected from (melamine-H)$^+$ of the formula (I-H), (melam-H)$^+$ of the formula (II-H), (guanamine-H)$^+$ of the formula (III-H), where R is methyl or phenyl, or [(amino)guanidine-H]$^+$ of the formula (IV-H), where R' is hydrogen or amino,

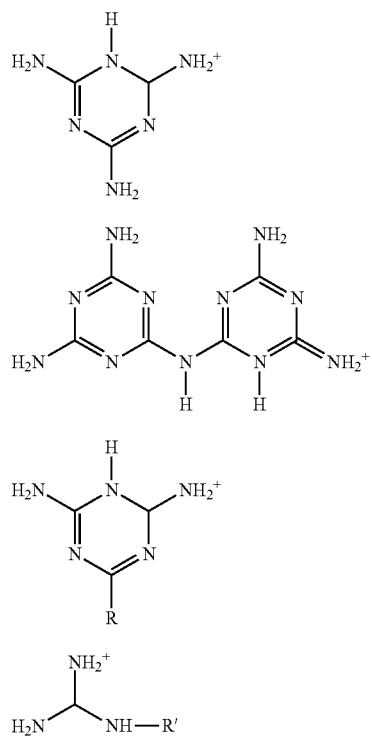

M=Cu, Mg, Ca, Zn, Mn, Fe, Co, Ni, TiO, ZrO, VO, B, Si, Al, Sb, La, Ti, Zr, Ce, Bi, or Sn, m=2 or 3, x and y are each, independently of one another, 0 or 1, p is an integer from 0 to 4 and z is an integer >5, where 1+m=3x+4y.

2. A composition comprising (i) an azine metal phosphate as claimed in claim 1, (ii) a metal-containing component different from the component (i), and (iii) optionally a metal-free component.

3. The composition as claimed in claim 2, characterized in that the metal-containing component (ii) is selected from metal hydroxide, metal phosphate, metal pyrophosphate, bismelamine zinc diphosphate, bismelamine magnesium diphosphate, bismelamine aluminum triphosphate, hydrotalcite, hydrocalumite, zeolite, cationically or anionically modified organoclay, stannate salt or molybdate salt, metal borate or metal phosphinate of the formula (V) or (VI), metal phosphonate of the formula (VII) or mixtures thereof,

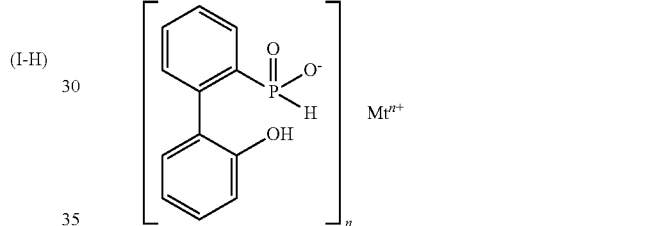

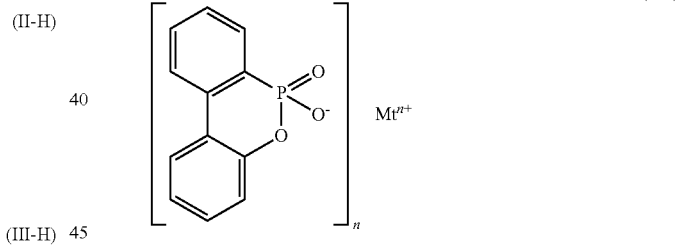

where R$^1$ and R$^2$ are each, independently of one another, hydrogen, linear or branched C$_1$-C$_6$-alkyl or phenyl; Mt$^1$=Ca, Mg, Zn, or Al, m=2 or 3, and Mt=Ca, Mg, Zn, Al, Sn, Zr, TiO, ZrO, Ce, MoO, WO$_2$, VO, Mn, Bi, or Sb, D=O or S, and n is 2 or 3.

4. The composition as claimed in claim 2, characterized in that the metal-free component (iii) is selected from red phosphorus, oligomeric phosphate ester, oligomeric phosphonate ester, cyclic phosphonate ester, thiopyrophosphoric ester, melamine orthophosphate, melam, melem, melamine phenyl phosphinate, monomeric, oligomeric or polymeric melamine phenyl phosphonate, ammonium polyphosphate, hydroxyalkylphosphine oxide, tetrakishydroxyalkylphosphonium salt, phospholane (oxide) derivative, dihydrophosphole (oxide) derivative, phosphinate ester, or mixtures thereof.

5. The composition as claimed in claim 4, characterized in that the oligomeric phosphate ester corresponds to the formula (VIII) or (IX), and/or the oligomeric phosphonate ester corresponds to the formula (X), (VIII)

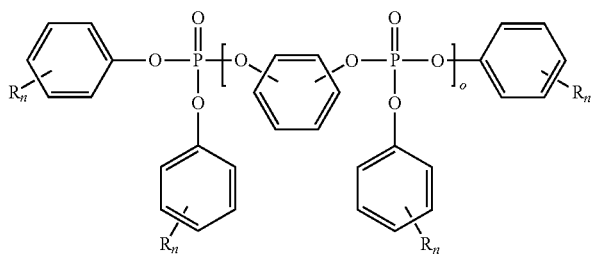

(IX)

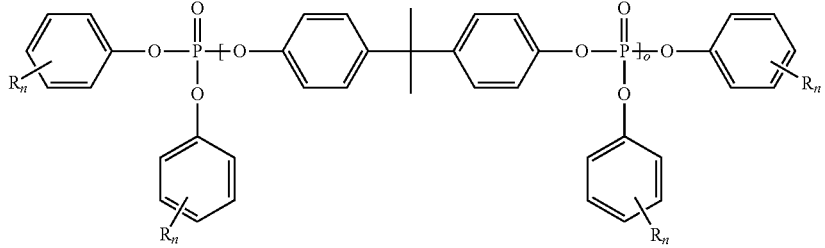

(X)

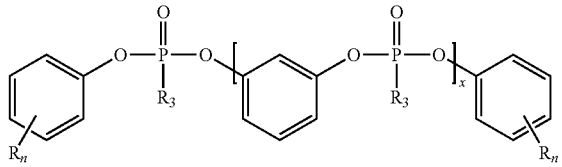

where each R is independently hydrogen, $C_1$-$C_4$-alkyl, or hydroxy, $R_3$ is methyl or phenyl, x is an integer from 1 to 20, n=1, 2, or 3, and o is an integer from 1 to 10.

6. The composition as claimed in claim 4, characterized in that the cyclic phosphonate ester corresponds to the formula (XI), (XI)

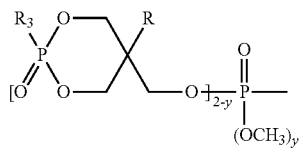

where R is hydrogen, $C_1$-$C_4$-alkyl, or hydroxy, $R_3$ is methyl or phenyl, and y=0 or 2.

7. The composition as claimed in claim 4, characterized in that the thiopyrophosphoric ester corresponds to the formula (XII), (XII)

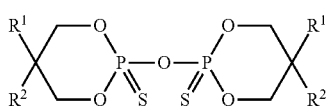

where each $R^1$ and $R^2$ is independently hydrogen, $C_1$-$C_4$-alkyl, or hydroxy.

8. The composition as claimed in claim 4, characterized in that the phosphinate ester is selected from a benzenemonophenyl ester derivative, a 9,10-dihydro-9-oxa-10-phosphaphenanthrene 10-oxide derivative or 6H-dibenzo(c,e)(1,2)oxaphosphorin-6-one derivative of the formula (XIII) or (XIV), 10-benzyl-9-oxa-10-phosphaphenanthrene 10-oxide, or mixtures thereof:

(XIII)

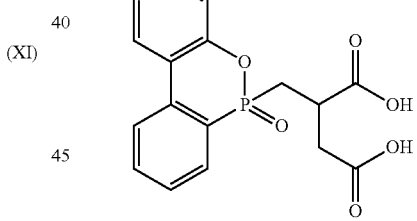

(XIV)

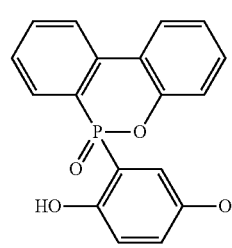

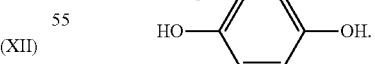

9. The composition as claimed in claim 2 further comprising a polymer or a polymer mixture, characterized in that the concentration of the sum of the components (i) and (ii) in the polymer or the polymer mixture is from 0.1 to 60% by weight, based on the polymer or the polymer mixture.

10. The composition as claimed in claim 9, characterized in that the polymer is a thermoplastic, a biopolymer based on polylactic acid and/or starch, a thermoset, or mixtures thereof.

11. A process for preparing azine metal phosphates of the general formula [I], $$[(A\text{-}H)^{(+)}[N^{m+}(PO_4)_x^{(3-)}(P_2O_7)_y^{(4-)}]^-\cdot pH_2O]_z \quad [I]$$

where (A-H)$^{(+)}$ is selected from (melamine-H)$^+$ of the formula (I-H), (melam-H)$^+$ of the formula (II-H), [(aceto)benzoguanamine-H]$^+$ of the formula (III-H), where R is methyl or phenyl, or [(amino)guanidine-H]$^+$ of the formula (IV-H), where R' is hydrogen or amino,

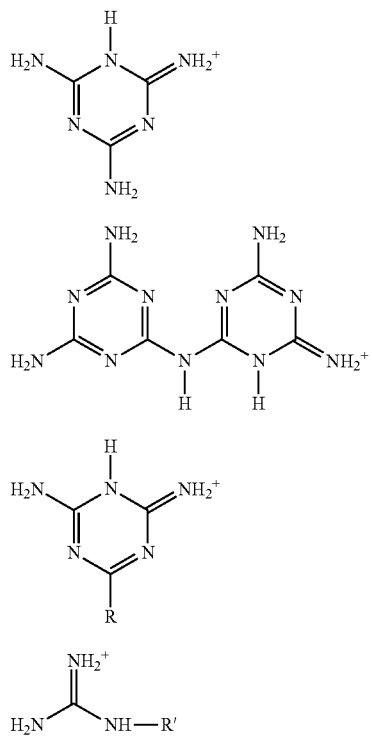

M=Cu, Mg, Ca, Zn, Mn, Fe, Co, Ni, TiO, ZrO, VO, B, Si, Al, Sb, La, Ti, Zr, Ce, Bi or Sn, m=2 or 3, x and y are each, independently of one another, 0 or 1, p is an integer from 0 to 4 and z is an integer >5, where 1+m=3x+4y, by reacting an azine starting material (A) with a metal oxide starting material (B) and orthophosphoric acid (C), wherein the azine starting material (A) is selected from melamine of the formula (I), melam of the formula (II), guanamine of the formula (III), or guanidine (bi)carbonate of the formula (IV), and the metal oxide starting material (B) is selected from metal oxides, metal hydroxides, metal carbonates, or a combination thereof,

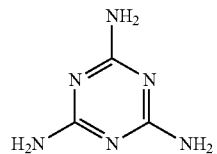

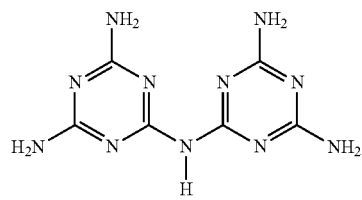

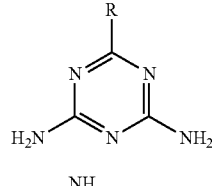

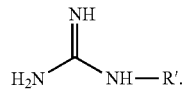

12. The process as claimed in claim 11, characterized in that the components (A) and (B) are initially charged as a mixture in water and orthophosphoric acid (C) is added.

13. The process as claimed in claim 11, characterized in that the reaction is carried out at from 20 to 90° C.

14. The process as claimed in claim 11, characterized in that the components (A):(B):(C) are present in a molar ratio of (1 to 3):(1):(1 to 3), with azine phosphates being additionally present outside the stoichiometry of 1:1:1.

15. The process as claimed in claim 11, characterized in that the reaction product is tempered at from 220 to 350° C.

16. The composition as claimed in claim 3, characterized in that the zeolite comprises zeolite X, zeolite Y, or a combination thereof.

17. The composition as claimed in claim 10, characterized in that the thermoplastic is selected from the group consisting of polyamide, polycarbonate, polyolefin, polystyrene, polyester, polyvinyl chloride, polyvinyl alcohol, acrylonitrile butadiene styrene (ABS), and polyurethane.

18. The composition as claimed in claim 10, characterized in that the thermoset is selected from the group consisting of epoxy resin, phenolic resin, melamine resin, and a combination thereof.

19. The process as claimed in claim 12, wherein the mixture is a suspension.

20. The process as claimed in claim 13, wherein the reaction is carried out at from 30 to 70° C.

* * * * *

UNITED STATES PATENT AND TRADEMARK OFFICE
CERTIFICATE OF CORRECTION

PATENT NO. : 9,505,793 B2
APPLICATION NO. : 14/436329
DATED : November 29, 2016
INVENTOR(S) : Wolfgang Wehner It is certified that error appears in the above-identified patent and that said Letters Patent is hereby corrected as shown below:

In the Claims

At Column 25, Line 20, delete:
"$[(A-H)^{(+)}[N^{m+}(PO_4)_x{}^{(3-)}(P_2O_7)_y{}^{(4-)}] \cdot pH_2O]_z$          [I]"

And insert:
--$[(A-H)^{(+)}[M^{m+}(PO_4)_x{}^{(3-)}(P_2O_7)_y{}^{(4-)}]^{(-)} \cdot pH_2O]_z$          [I]--.

At Column 25, Line 30, delete:

"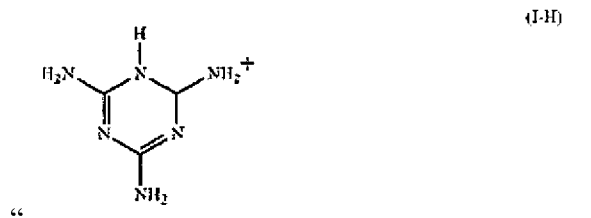          (I-H)"

And insert:

--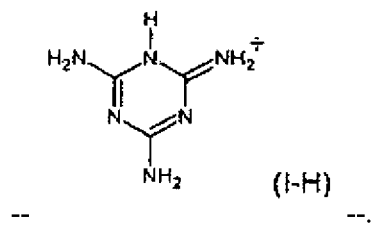     (I-H)--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,505,793 B2

At Column 25, Lines 45-55, delete:

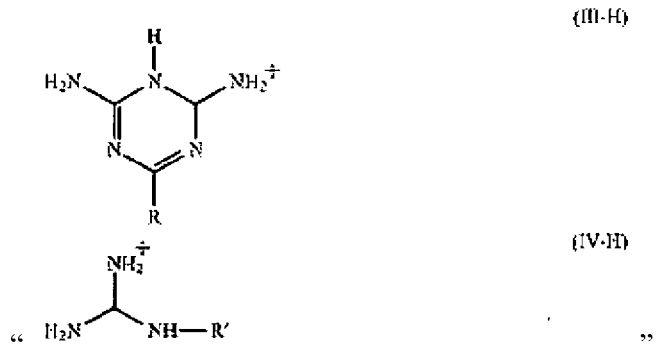

And insert:

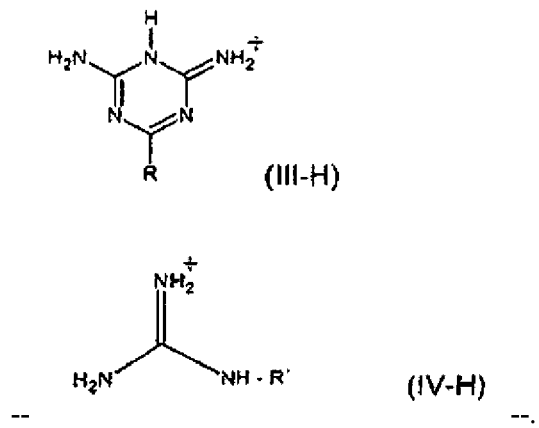

--    --.

At Column 26, Line 16, after "formula (VII)" insert --,--.

At Column 29, Line 3, delete:
"$[(A-H)^{(+)}[N^{m+}(PO_4)_x{}^{(3-)}(P_2O_7)_y{}^{(4-)}]\cdot pH_2O]_z$       [I]"

And insert:
--$[(A-H)^{(+)}[M^{m+}(PO_4)_x{}^{(3-)}(P_2O_7)_y{}^{(4-)}]^{(-)}\cdot pH_2O]_z$       [I]--.

At Column 29, Line 42, after "Bi" insert --,--.